(12) United States Patent
Thuemen et al.

(10) Patent No.: US 12,029,388 B2
(45) Date of Patent: Jul. 9, 2024

(54) ENDOSCOPE

(71) Applicant: Olympus Winter & Ibe GmbH, Hamburg (DE)

(72) Inventors: Alrun Thuemen, Hamburg (DE); Jens Schnitger, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 467 days.

(21) Appl. No.: 17/407,492

(22) Filed: Aug. 20, 2021

(65) Prior Publication Data

US 2021/0378489 A1 Dec. 9, 2021

Related U.S. Application Data

(63) Continuation of application No. PCT/EP2020/054994, filed on Feb. 26, 2020.

(30) Foreign Application Priority Data

Mar. 5, 2019 (DE) ...................... 10 2019 105 564.4

(51) Int. Cl.
*A61B 1/00* (2006.01)

(52) U.S. Cl.
CPC ...... *A61B 1/00124* (2013.01); *A61B 1/00066* (2013.01); *A61B 1/00073* (2013.01)

(58) Field of Classification Search
CPC ............ A61B 1/00124; A61B 1/00066; A61B 1/00073

See application file for complete search history.

(56) References Cited

U.S. PATENT DOCUMENTS

2002/0062082 A1 5/2002 Ohara et al.
2009/0093725 A1* 4/2009 Sato ........................ H05K 1/147
                                                              600/462

(Continued)

FOREIGN PATENT DOCUMENTS

DE  10 2007 009 292 A1  8/2008
DE  10 2017 102 178 B3  6/2018

(Continued)

OTHER PUBLICATIONS

International Search Report dated May 29, 2020 received in PCT/EP2020/054994.
English abstract only of EP 1 958 564 A2.

*Primary Examiner* — Howard D Brown, Jr.
(74) *Attorney, Agent, or Firm* — Scully, Scott, Murphy & Presser, P.C.

(57) ABSTRACT

An endoscope including: a retaining body; and a flexible printed circuit board providing an electrical connection between an electrical component arranged in a proximal end region of the endoscope and an internal electrical terminal provided in the proximal end region distanced along a longitudinal axis from the electrical component. The flexible printed circuit board includes: a first circuit board section extending in a longitudinal axial direction and guided at least partially in a cavity in the endoscope by the electrical terminal in the direction of the electrical component, and a second circuit board section arranged on the retaining body and guided along a lower side of the retaining body directed in a direction of an internal space in the endoscope and along an upper side of the retaining body directed in a direction of an outer sleeve of the endoscope towards the electrical component, and electrically contacts the electrical component.

22 Claims, 5 Drawing Sheets

(56) References Cited

U.S. PATENT DOCUMENTS

| | | | |
|---|---|---|---|
| 2017/0105612 A1* | 4/2017 | Wieters | A61B 1/0011 |
| 2018/0317756 A1 | 11/2018 | Unsai | |
| 2019/0067891 A1 | 2/2019 | Kubon et al. | |
| 2021/0007584 A1* | 1/2021 | Heni | A61B 1/00128 |
| 2021/0282628 A1* | 9/2021 | Tortola | A61B 1/0669 |

FOREIGN PATENT DOCUMENTS

| | | |
|---|---|---|
| WO | 2007/092533 A2 | 8/2007 |
| WO | 2014/160983 A2 | 10/2014 |
| WO | WO-2014160983 A2 * 10/2014 | ......... A61B 1/00009 |

* cited by examiner

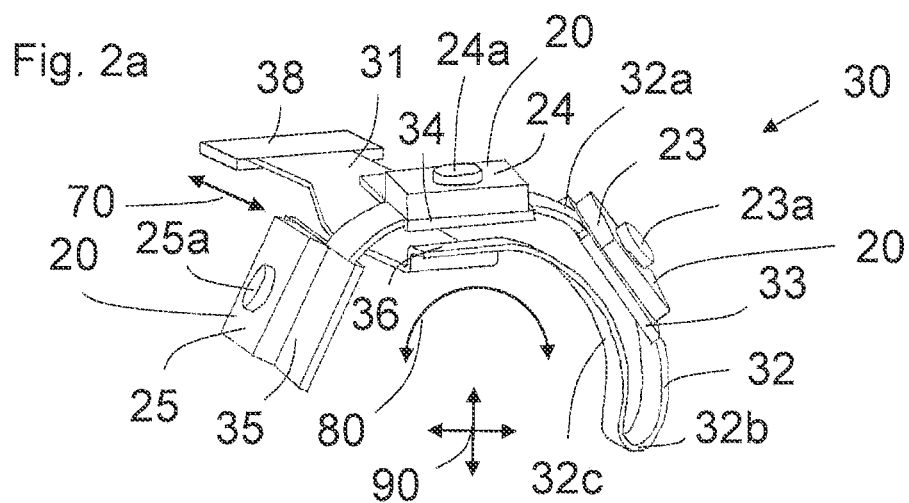
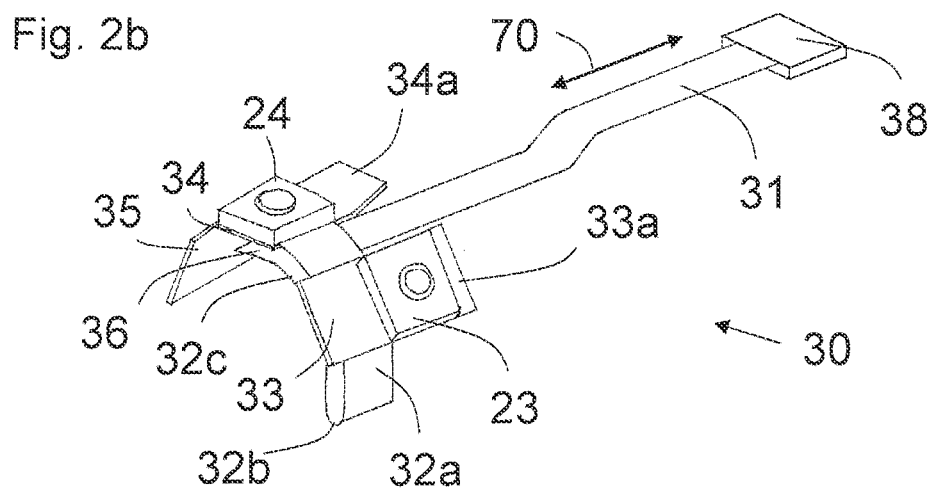

ENDOSCOPE

CROSS-REFERENCE TO RELATED APPLICATION

The present application is a continuation of PCT/EP2020/054994 filed on Feb. 26, 2020, which is based upon and claims the benefit to DE 10 2019 105 564.4 filed on Mar. 5, 2019, the entire contents of each of which are incorporated herein by reference.

BACKGROUND

Field

The present disclosure relates to an endoscope and more particularly to an endoscope comprising a dimensionally-stable retaining body and an elongated, flexible printed circuit board which provides an electrical connection between at least one electrical component arranged in a proximal end region of the endoscope and an internal electrical terminal provided in the proximal end region.

Prior Art

Medical endoscopes comprise at their proximal end region, for example at the handle or close to the handle, many switches for selecting or controlling various functions of the endoscope. Conventionally, such switches are soldered to a wider section of a flexible printed circuit board. The wider section of the flexible printed circuit board is frequently fixed by means of a retaining element to a tubular element, for example by means of screws. Proceeding from the wider section, the flexible printed circuit board is guided through an opening into a cavity in the endoscope, for example, an intermediate space between the two tubular elements, in which the flexible printed circuit board extends in a longitudinal axial direction to the electrical terminal.

It has however been revealed that the possibility exists that the functioning of switches which are contacted by means of the aforementioned electrical connection to the electrical terminal decreases due to aging since the switches can be lifted off of the wider section of the flexible printed circuit board. Moreover, the described electrical connection requires a large installation space.

SUMMARY

An object is to provide an endoscope with an enhanced electrical connection between an electrical component and an electrical terminal arranged in an endoscope's interior.

Such object can be solved by an endoscope comprising a dimensionally-stable retaining body and an elongated flexible printed circuit board which provides an electrical connection between at least one electrical component arranged in a proximal end region of the endoscope and an internal electrical terminal provided in the proximal end region that is distanced along the longitudinal axis from at least one electrical component, wherein a first circuit board section of the flexible printed circuit board extending in the longitudinal axial direction of the endoscope is received at least partially in a cavity in the endoscope by the electrical terminal in the direction of the at least one electrical component, wherein a second circuit board section arranged on the retaining body is guided along a lower side of the retaining body directed in the direction of an internal space in the endoscope and along an upper side of the retaining body directed in the direction of an outer sleeve of the endoscope towards the electrical component, and electrically contacts the electrical component.

The flexible printed circuit board can comprise two printed circuit board sections. The first printed circuit board section extends in a longitudinal axial direction and is guided from the electrical terminal to the retaining body. The second printed circuit board section is guided on the upper side and lower side of the retaining body and is electrically contacted with the electrical component.

Installation space in the longitudinal axial direction can be saved when the electrical component is moved in a longitudinal actual direction, such as toward the opening of the cavity from which the flexible printed circuit board coming from the electrical terminal exits. If the electrical component is however positioned too close to the opening in the longitudinal axial direction, the difficulty arises of guiding the flexible printed circuit board to the electrical component without too strongly kinking the flexible printed circuit board, which can impair the reliability of the electrical contact.

Guiding the printed circuit board section along the upper side and the lower side of the retaining body allows the flexible printed circuit board to be guided, starting from the opening in the cavity, along a detour to the electrical component, and no longer directly. This has the advantage that the electrical component can be moved much closer in the longitudinal axial direction toward the opening, or even in a radial direction of the endoscope above or below the opening. Installation space is thereby saved in the longitudinal axial direction.

Moreover, guiding the second printed circuit board section along the upper side and lower side of the retaining body allows the at least one electrical component to be safely and reliably fastened to the flexible printed circuit board. The detour along the upper side and lower side of the retaining body prevents the flexible printed circuit board from having to be strongly kinked after exiting the opening in the cavity in order to contact the electrical component. This keeps the electrical contact between the at least one flexible printed circuit board and the at least one electrical component from disconnecting, for example during an endoscope preparation process.

The flexible printed circuit board can have the shape of a flat strip. A flexible printed circuit board so configured can save space, can be enclosed effectively in a lateral direction, and can offer a large surface for contacting the at least one electrical component.

The at least one electrical component can be mechanically connected directly to the second printed circuit board section, such as by means of a soldered connection. By means of a soldered connection, the at least one electrical component can be fixed both mechanically and contacted electrically.

The cavity can have an opening, such as being oriented in a radial direction, through which the first printed circuit board section is guided out of the cavity. A transitional region of the first printed circuit board section to the second printed circuit board section can be arranged adjacent to the opening. The cavity in which the first printed circuit board section is at least partially accommodated can be an intermediate space between a casing tube and a fiber tube.

In the context of the present description, the terms longitudinal axial direction, peripheral direction and radial direction refer to the reference system of the endoscope.

The second printed circuit board section can comprise an upper subsection guided on the upper side of the retaining body and a lower subsection guided on the lower side of the retaining body that extend at least partially in opposite directions.

Since the upper subsection and the lower subsection are guided in opposite directions, this can allow one of the subsections to be guided away from the opening in the cavity, and the other subsection can be returned to the electrical component arranged radially above or below the opening. The second printed circuit board section can describe a circular arc along the surface of the retaining body with which a radial distance between the opening and the electrical component is bridged without the flexible printed circuit board having to be excessively angled or kinked.

The upper subsection and the lower subsection can each be guided in opposite peripheral directions of the endoscope.

By guiding the upper and lower subsection in a peripheral direction, no installation space is needed for guidance in the longitudinal axial direction. Instead, installation space can be exploited in the peripheral direction of the endoscope in order to guide the flexible printed circuit board to the electrical component.

The second printed circuit board section can comprise a lateral subsection that is guided along a side edge of the retaining body, such as facing the peripheral direction, and connects the upper subsection to the lower subsection.

The guidance along the side edge can prevent the flexible printed circuit board from being twisted between the upper subsection and the lower subsection.

The side edge of the retaining body along which the lateral subsection is guided can be rounded. This can prevent a strong bend or curvature of the flexible printed circuit board. The side edge can adjoin the retaining body in the peripheral direction. Moreover, the lateral subsection can also connect the upper subsection to the lower subsection in a radial direction.

According to one embodiment, the upper subsection can be mechanically connected to the electrical component, wherein the upper subsection electrically contacts the electrical component, wherein the lower subsection is directly connected to the first printed circuit board section.

The flexible printed circuit board according to this embodiment can abut the retaining body as follows: The first printed circuit board section extends in a longitudinal axial direction from the electrical terminal in the intermediate space to the lower side of the retaining body. The bottom subsection of the second printed circuit board section adjoins the first printed circuit board section and is guided on the lower side of the retaining body, such as in a peripheral direction. If applicable, the lateral subsection can extend on the side edge of the retaining body and can be guided substantially in a radial direction and connect the lower subsection to the upper subsection. The upper subsection can be guided on the upper side of the retaining body, such as in a peripheral direction, and can be mechanically connected to and electrically contact the electrical component.

The electrical component in this embodiment can be arranged in a radial direction above the retaining body. The electrical component can therefore be easily coupled to a control element arranged on an outer sleeve of the endoscope.

According to one embodiment, at least three electrical components can be included that are mechanically connected to, and electrically contact, the upper subsection at a distance from each other in the peripheral direction.

The first printed circuit board section can include an angle of 60° to 120°, such as between 80° to 100°, with the second printed circuit board section, such as with the lower subsection of the second printed circuit board section, at a transitional region from the first printed circuit board section to the second printed board section.

At the transitional region between the first printed circuit board section and the second printed board section, the flexible printed board accordingly has an angle. The direction of extension of the flexible printed circuit board changes at this transitional region such as from the longitudinal axial direction to the peripheral direction. This angle can be a right angle.

The flexible printed circuit board can be a single piece. The transitional region can be a flat printed circuit board section that lies flat on a planar element, such as the casing tube, and the first printed circuit board section can branch off from there in a longitudinal axial direction, and the second printed circuit board section can branch off from there in a peripheral direction. To achieve the angle, strong kinking or bending of the flexible printed circuit board can therefore be advantageously unnecessary.

The second printed circuit board section can comprise at least one dimensionally-stable receiving surface to which the at least one electrical component is directly mechanically connected and electrically contacted, wherein the at least one dimensionally-stable receiving surface can be configured as part of the upper subsection, or can be fixed to the upper subsection.

By means of the at least one dimensionally-stable receiving surface, a stable surface can be provided for receiving the at least one electrical component. The at least one electrical component can be soldered to the at least one dimensionally-stable receiving surface. A secure fixation and an electrical contacting of the electrical component can thereby be simultaneously achieved. The at least one dimensionally-stable receiving surface can be arranged on a flat support surface of the retaining body.

According to one embodiment, the upper subsection can comprise three dimensionally-stable receiving surfaces that are distanced from each other in the peripheral direction and are connected to each other by means of flexible intermediate sections of the upper subsection. An electrical component can be fixed to each of these receiving surfaces.

The at least one dimensionally-stable receiving surface can have an insertion region extending in the longitudinal axial direction of the endoscope which can be inserted into a pocket of the retaining body to fix the flexible printed circuit board on the retaining body, wherein the pocket can enclose the insertion region in a peripheral direction and/or radial direction.

The insertion region can extend in a longitudinal axial, such as proximal, direction beyond the flexible sections of the second printed circuit board section. Accordingly, the insertion region can be inserted in a longitudinal axial direction to fix the flexible printed circuit board in the pocket of the retaining body.

Advantageously, the insertion region can permit easy, tool-free and reliable installation of the flexible printed circuit board without screws. Enclosing the insertion regions in a longitudinal axial direction and/or peripheral direction can prevent the at least one dimensionally-stable receiving region and hence the at least one electrical component from slipping.

The retaining body can have a proximal section that extends outward in a radial direction beyond the support surfaces of the retaining body. In this proximal section, at least one cutout can be provided that, together with the at least one support surface, forms the pocket.

The retaining body can have a cross-section in the form of a circular arc, wherein the circular arc can have a center angle of 185° to 270°.

The center angle is an angle that on the one hand extends from a connecting line between the circular arc midpoint and a first endpoint of the circular arc, and on the other hand from a connecting line between the ark midpoint and a second endpoint of the circular arc. Given the configuration of the retaining body with a circular arc-shaped cross-section, the retaining body can be advantageously fixed easily and securely on a tubular element, and the casing tube can be arranged thereunder. By selecting the center angle within a range of 185° to 270°, the retaining body can hold securely to the retaining element since it encloses it by more than one-half.

The retaining body can include a groove running along the upper side, and/or the lower side, and/or the side edge in the peripheral direction of the endoscope in which the second printed circuit board section can be at least partially accommodated. By means of the groove, the second printed circuit board section can be securely held, and slippage in the longitudinal axial direction can be prevented.

The at least one electrical component can be an electrical switch. In the context of the present description, the term switch is understood to mean both switches that remain in the switched-on state after they are actuated as well as switches that return to their initial state after they are actuated, i.e., buttons.

BRIEF DESCRIPTION OF THE DRAWINGS

Further features will become apparent from the description of embodiments together with the claims and the attached drawings. Embodiments can fulfill individual features or a combination of several features.

The embodiments are described below, without restricting the general idea of the invention, based on exemplary embodiments in reference to the drawings, whereby we expressly refer to the drawings with regard to all details that are not explained in greater detail in the text. In the figures:

FIG. 2a illustrates a schematic and simplified perspective representation of a flexible printed circuit board with three switches, FIG. 2b illustrates a schematic and simplified perspective representation of a flexible printed circuit board with three switches.

In the drawings, the same or similar elements and/or parts are always provided with the same reference numbers; a reintroduction will therefore always be omitted.

DETAILED DESCRIPTION

Figure 1:
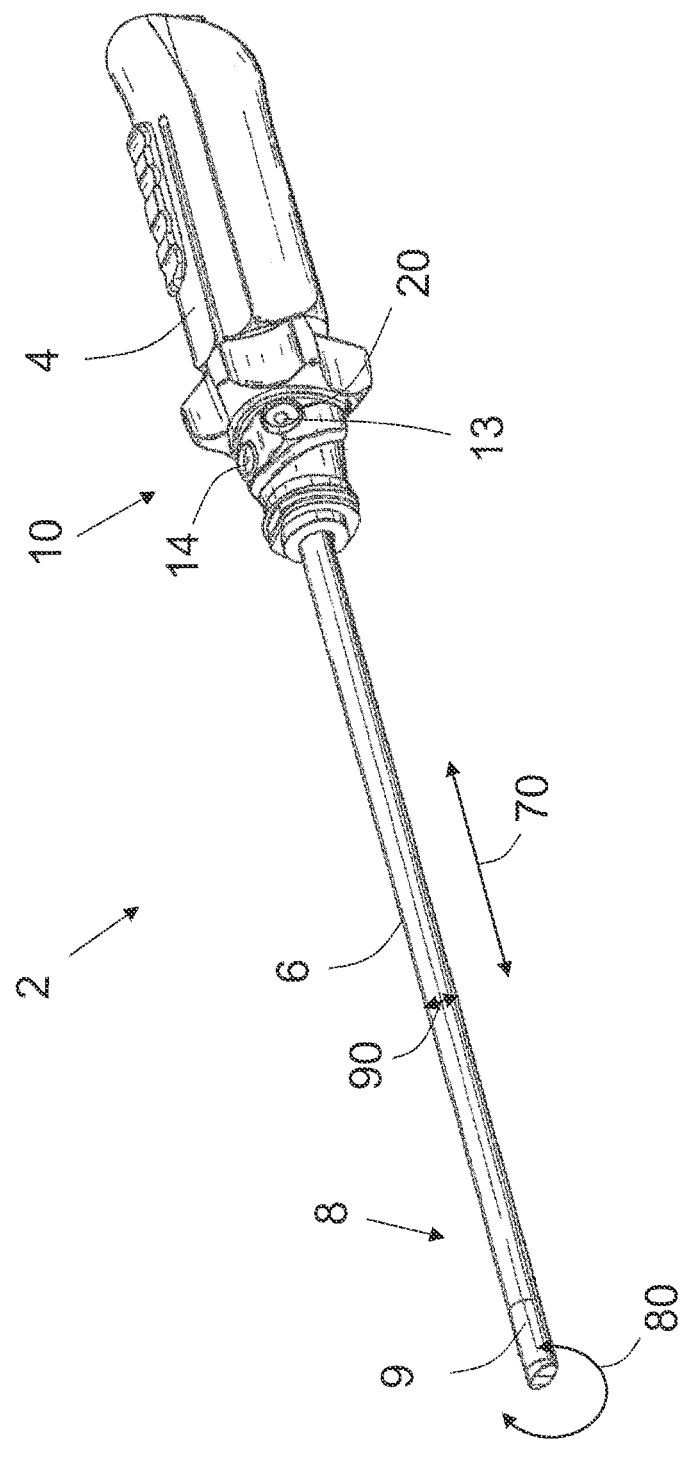
FIG. 1 illustrates a schematic and simplified perspective representation of an endoscope.

FIG. 1 shows an example of an embodiment of an endoscope 2. The endoscope 2 comprises a handle 4 and a shaft 6 that for example can be inserted into the interior of a patient's body. An optical system 9 is arranged in a distal end section 8 of the endoscope with which an image of an object space in front of the endoscope 2 is captured, and information from the image is forwarded in the direction of the proximal end section 10.

A longitudinal axial direction 70 of the endoscope 2 extends in the direction of the longitudinal axis of the shaft 6. A peripheral direction 80 orthogonal thereto runs in the direction of the circumference of the shaft 6, and a radial direction 90 orthogonal to the longitudinal axial direction 70 and the peripheral direction 80 runs in the radial direction of the shaft 6.

In order to change parameters of the endoscope 2 while using the endoscope 2, for example settings with respect to the recording and reproduction of the image, control elements 13, 14 are arranged on the handle 4. A third control element is arranged at a distance from the control elements 13, 14 in a peripheral direction and is concealed given the perspective in FIG. 1. These control elements 13, 14 can be actuated by a finger of a hand while such hand grasps the handle 4. This allows the endoscope 2 to be operated with a single hand. In the shown embodiment, the control elements 13, 14 are buttons that are pressed for actuation.

In order to give the control elements 13, 14 the desired functionality, a signal that is generated when actuating the control elements 13, 14 is forwarded to an electrical terminal in the endoscope's interior that transmits the signal for example to a control system of the endoscope.

The signal is forwarded by means of a flexible printed circuit board 30 as shown in a schematically simplified form in FIGS. 2a and 2b in an exemplary embodiment. The selected representation shows a flexible printed circuit board 30 in the form in which it is arranged in the interior of endoscope 2. Curvatures in the flexible printed circuit board 30 therefore arise from guiding the printed circuit board 30 in the endoscope 2 and are therefore not a consequence of a reinforcement of the printed circuit board 30 in the curved regions.

Three electrical components 20 are arranged on the printed circuit board 30 which, in the shown embodiment, are electrical switches 23, 24, 25 with contact buttons 23a, 24a, 25a. The switches 23, 24, 25 are arranged in the endoscope's interior such that they are coupled to the control elements 13, 14. If one of the control elements 13, 14 is actuated, pressure is exerted on the contact button 23a, 24a, 25a arranged under the control element 13, 14, and the pressure is converted into an electrical signal by means of the particular switch 23, 24, 25.

The switches 23, 24, 25 are fixed and contacted to dimensionally-stable receiving surfaces 33, 34, 35 of the flexible printed circuit board 30, for example by means of a soldered connection. In this manner, the electrical signals are transmitted to the flexible printed circuit board 30.

The flexible printed circuit board 30 comprises a first printed circuit board section 31 that extends in a longitudinal axial direction 70 and is connected to an electrical terminal 38 shown schematically in FIG. 2b, as well as a second printed circuit board section 32. The first printed circuit board section 31 is curved at two places in the shown embodiment so that a middle region of the first printed circuit board section lies radially deeper than the other regions. This middle region is guided in a cavity in the endoscope 2, for example in an intermediate space between a casing tube and a fiber tube.

The second printed circuit board section 32 is divided into an upper subsection 32a, a lateral subsection 32b and a lower subsection 32c. The upper subsection 32a extends in a peripheral direction 80 and comprises the dimensionally-stable receiving surfaces 33, 34, 35 that are arranged offset from each other in a peripheral direction 80 along the upper subsection 32a. The lateral subsection 32b connects the upper subsection 32a in a radial direction 90 to the lower subsection 32c. The lower subsection runs in a peripheral direction 80 and is connected to the first printed circuit board section 31 in a transitional region 36. In the transitional region 36, the first printed circuit board section 31 and the second subsection 32c enclose a right angle.

By means of the shown guidance of the second printed circuit board section 32, it is possible to arrange the electrical components 20 in a radial direction 90 above the transitional region 36 so that, to connect the electrical components 20, no additional installation space in the longitudinal axial direction 70 is needed.

FIG. 2b shows the printed circuit board 30 from a different perspective than in FIG. 2a. In this view, the longitudinal axial extension of the first printed circuit board section 31 and the electrical connection 38 are easily discernible.

Moreover, the shape of the dimensionally-stable receiving surfaces 33, 34, 35 are readily visible. The dimensionally-stable receiving surfaces 33, 34, 35 each have a flat shape that extends in a longitudinal axial direction 70 and in a peripheral direction 80. In the longitudinal axial direction 70, the dimensionally-stable receiving surfaces 33, 34, 35 each comprise an insertion region 33a, 34a that projects beyond the remaining regions of the second printed circuit board section 32 in a longitudinal axial direction 70.

Figure 3A:
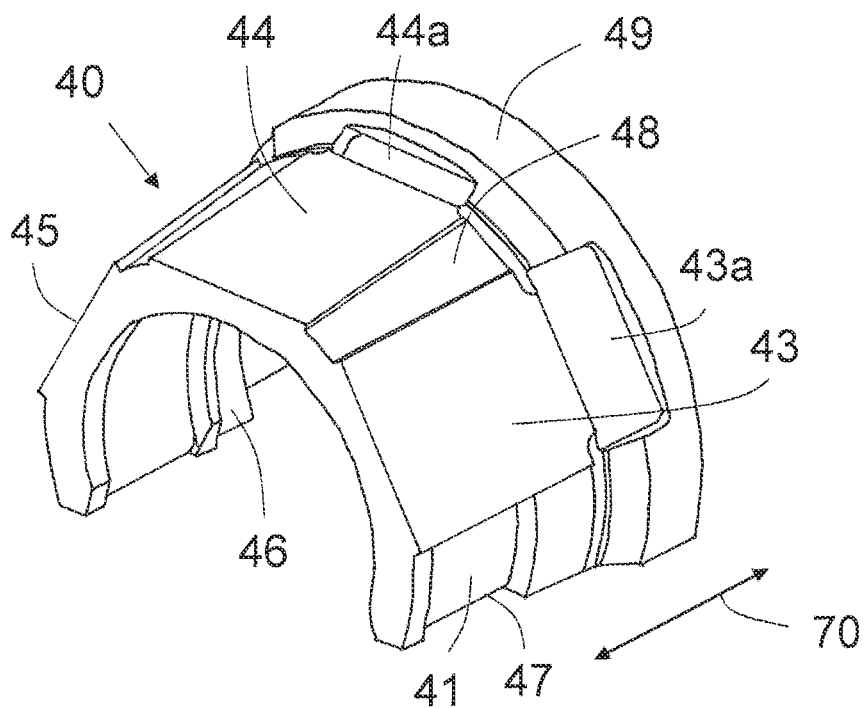
FIG. 3a illustrates a schematic and simplified perspective representation of a retaining body and a flexible printed circuit board.

FIG. 3a shows a schematically simplified retaining body 40. The retaining body 40 has a circular arc-shaped cross-section with a center angle of at least 185° so that it securely holds to a tubular element lying thereunder whose outer circumference basically corresponds to the inner circumference of the retaining body 40.

A groove 41 is introduced in an upper side, 48, a side edge 47, and a lower side 46 of the retaining body 40 for guiding the second printed circuit board section 32. The upper side 48 has three flat support surfaces 43, 44, 45 on which the receiving surfaces 33, 34, 35 can be arranged. The radius of the cross-section of the retaining body 40 is enlarged in a proximal section 49. In this proximal section, cutouts are provided that, together with the support surfaces 43, 44, 45, form pockets 43a, 44a for the dimensionally-stable receiving surfaces 33, 34, 35.

Figure 3B:
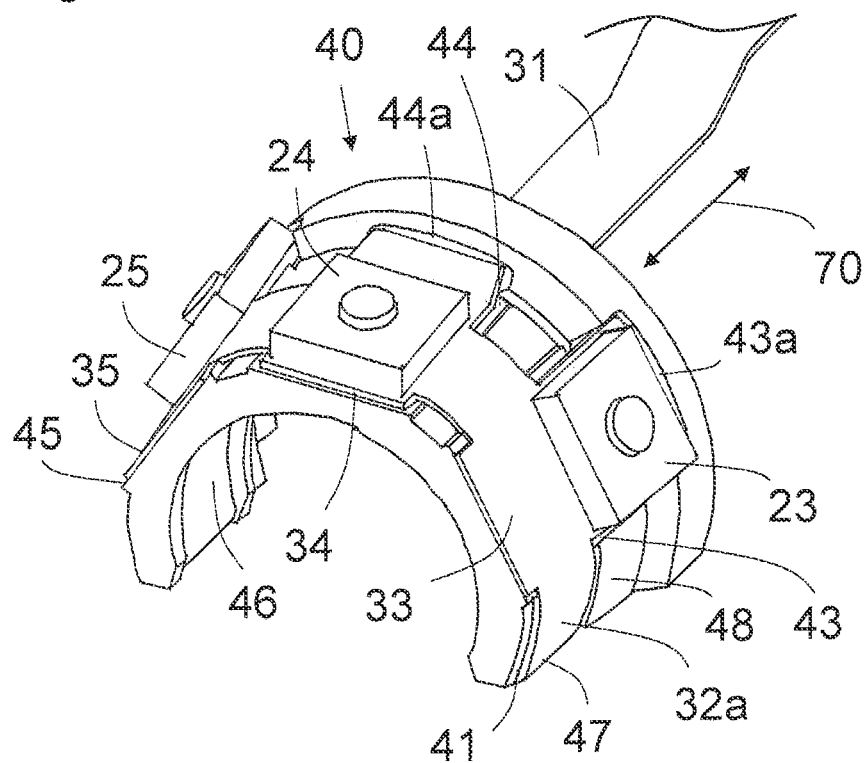
FIG. 3b illustrates a schematic and simplified perspective representation of a retaining body and a flexible printed circuit board.

FIG. 3b shows in a schematically simplified manner the retaining body 40 from FIG. 3a together with the flexible printed circuit board 30. The subsections 32a, 32b, 32c of the second printed circuit board section 32 abut the retaining body 40 and are at least partially accommodated in the groove 41. Due to the groove 41, slippage of the second printed circuit board section 32 in the longitudinal axial direction 70 is therefore prevented. The dimensionally-stable receiving surfaces 33, 34, 35 abut the support surfaces 43, 44, 45 of the retaining body 40. The insertion regions 33a, 34a are accommodated in the pockets 43a, 44a, and are each held partially at the lower side by the support surfaces 43, 44, 45 and at the top side by the proximal section 49 of the retaining body 40. By inserting the insertion regions 33a, 34a into the pockets 43a, 44a, the flexible printed circuit board 30 can therefore be easily and securely fixed to the retaining body 40 without screws.

Figure 4:
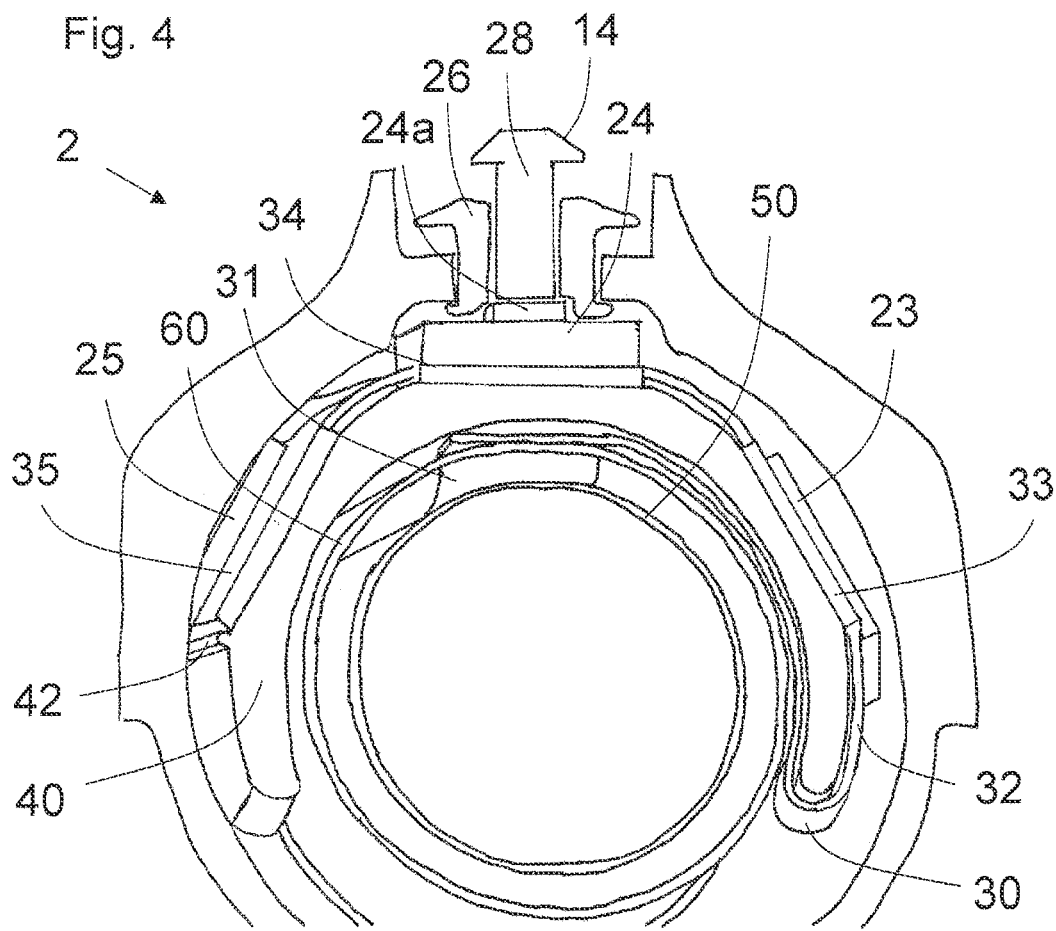
FIG. 4 illustrates a schematic and simplified perspective section through a proximal end section of an endoscope.

FIG. 4 shows a schematically simplified perspective section through an endoscope 2. The section runs through the longitudinal axial section of the retaining body 40 in which the groove 41 and the switch 24 are arranged. In this representation, it can be seen how the switches 23, 24, 25, the flexible printed circuit board 30 and the retaining body 40 are arranged in the endoscope 2.

The switch 24 is arranged below a plunger 28 which is guided in a dome 26. The plunger 28 and the dome 26 are part of the control element 14. If the control element 14 is actuated, the plunger 28 is pressed downward onto the contact button 24a of the switch 24, and an electrical signal is transmitted to the printed circuit board 30. The switches 23, 24, 25 are each arranged on the dimensionally-stable receiving surfaces 33, 34, 35.

The retaining body 40 encompasses a casing tube 60 lying to the inside in a radial direction. In the representation in FIG. 4, the rotating body 40, at least in part, does not directly abut the casing tube 60 since the shown section runs through the groove 41, and space must remain between the retaining body 40 and casing tube 60 for guiding the lower subsection 32c. In the embodiment shown in FIG. 4, the retaining body has a projection 42 against which the dimensionally-stable receiving surface 35 abuts in the peripheral direction 80.

A fiber tube 50 is arranged within the casing tube 60. The first printed circuit board section 31 is guided in a longitudinal axial direction between the casing tube 60 and the fiber tube 50.

Figure 5:
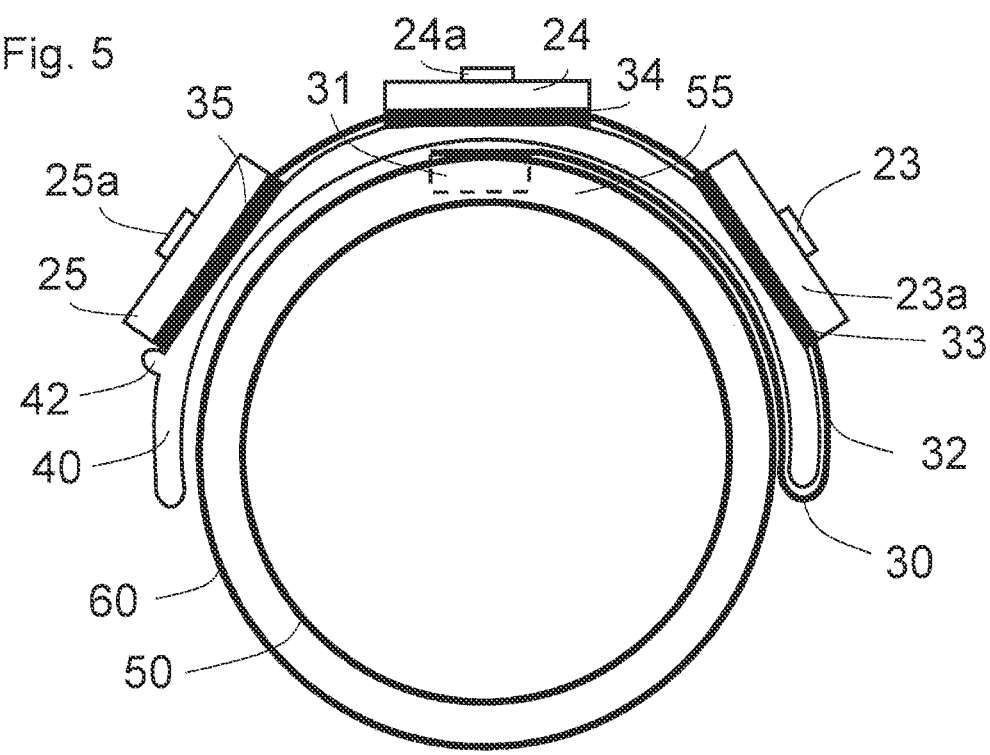
FIG. 5 illustrates a schematic and simplified cross-section through a proximal end section of an endoscope.

FIG. 5 shows a schematically simplified cross-sectional view of the section from FIG. 4. In this representation, the guidance of the second printed circuit board section 32 on the retaining body 40 is easily recognizable. The first printed board section 31 is guided through an opening in the casing tube 60, for example a cutout, located behind the image plane in the intermediate space 55 between the casing tube 60 and fiber tube 50.

Figure 6:
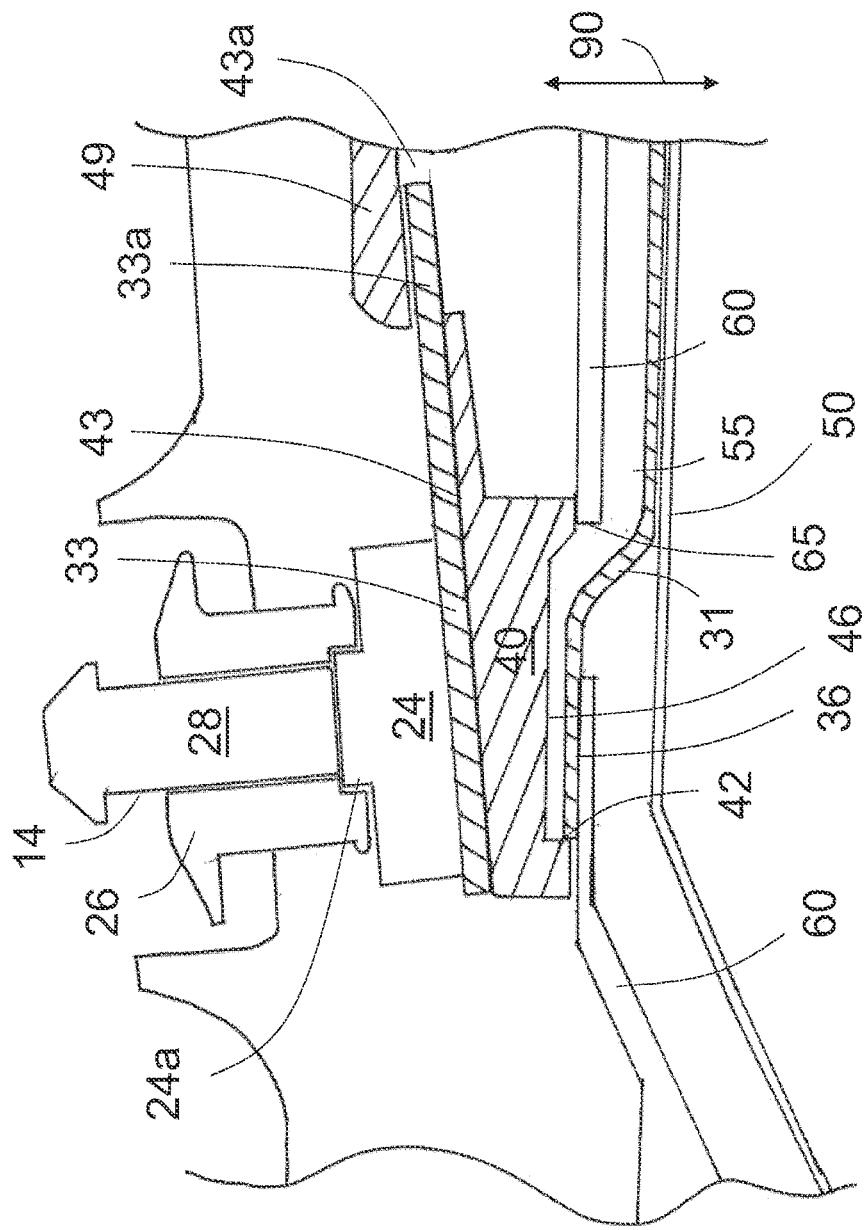
FIG. 6 illustrates a schematic and simplified longitudinal section through a proximal end section of an endoscope.

FIG. 6 shows a longitudinal section through the endoscope 2 in a region of the control element 14 and the transitional region 36. In this view, the flexible printed circuit board 30 is emphasized by hatching from bottom left to top right, and the retaining body 40 is emphasized by hatching from top left to bottom right. It is shown that the insertion region 33a of the dimensionally-stable receiving surface 33 is inserted into the pocket 43a of the retaining body 40.

On the lower side 46 of the retaining body 40, the flexible printed circuit board is guided in the groove 42. Proceeding from the transitional region 36 in a proximal direction, i.e., to the right in FIG. 6, the first printed circuit board section 31 is guided through an opening 65 in the casing tube 60 in the intermediate space 55 between the casing tube 60 and fiber tube 50. In this intermediate space 55, the first printed circuit board section 31 runs to the electrical terminal 38 which is not shown in FIG. 6.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

2 Endoscope
4 Handle
6 Endoscope shaft
8 Distal end region
9 Optical system

10 Proximal end region
13 Control element
14 Control element
20 Electrical component
23 Electrical switch
23a Contact button
24 Electrical switch
24a Contact button
25 Electrical switch
25a Contact button
26 Dome
28 Plunger
30 Flexible printed circuit board
31 First printed circuit board section
32 Second printed circuit board section
32a Upper subsection
32b Lateral subsection
32C Lower subsection
33 Dimensionally-stable receiving surface
33a Insertion region
34 Dimensionally-stable receiving surface
34a Insertion region
35 Dimensionally-stable receiving surface
36 Transitional region
38 Electrical terminal
40 Retaining body
41 Groove
42 Projection
43 Support surface
43a Pocket
44 Support surface
44a Pocket
45 Support surface
46 Lower side
47 Side edge
48 Upper side
49 Proximal section
50 Fiber tube
55 Intermediate space
60 Casing tube
65 Opening
70 Longitudinal axial direction
80 Peripheral direction
90 Radial direction

What is claimed is:

1. An endoscope comprising:
a dimensionally-stable retaining body; and
an elongated, flexible printed circuit board which provides an electrical connection between at least one electrical component arranged in a proximal end region of the endoscope and an internal electrical terminal provided in the proximal end region that is distanced along a longitudinal axis from the at least one electrical component,
wherein the flexible printed circuit board comprises:
a first circuit board section extending in a longitudinal axial direction of the endoscope and guided at least partially in a cavity in the endoscope by the electrical terminal in the direction of the at least one electrical component, and
a second circuit board section arranged on the retaining body and guided along a lower side of the retaining body directed in a direction of an internal space in the endoscope and along an upper side of the retaining body directed in a direction of an outer sleeve of the endoscope towards the at least one electrical component, and electrically contacts the at least one electrical component; and
wherein the upper side of the retaining body is an outer peripheral surface of the retaining body and the lower surface of the retaining body is an inner peripheral surface of the retaining body.

2. The endoscope according to claim 1, wherein the second printed circuit board section comprises an upper subsection guided on the upper side of the retaining body and a lower subsection guided on the lower side of the retaining body, the upper and lower subsections extend at least partially in opposite directions.

3. The endoscope according to claim 2, wherein the upper subsection and the lower subsection are each guided in opposite peripheral directions of the endoscope.

4. The endoscope according to claim 2, wherein the second printed circuit board section comprises a lateral subsection that is guided along a side edge of the retaining body and connects the upper subsection to the lower subsection.

5. The endoscope according to claim 4, wherein the lateral subsection faces a peripheral direction.

6. The endoscope according to claim 2, wherein the upper subsection is mechanically connected to the electrical component, the upper subsection electrically contacts the electrical component, and the lower subsection is directly connected to the first printed circuit board section.

7. The endoscope according to claim 1, wherein the first printed circuit board section includes an angle of 60° to 120° with the second printed circuit board section at a transitional region from the first printed circuit board section to the second printed board section.

8. The endoscope according to claim 7, wherein the first printed circuit board section includes the angle of 80° to 100° with the second printed circuit board section at the transitional region.

9. The endoscope according to claim 7, wherein the first printed circuit board section includes the angle of 60° to 120° with the lower subsection of the second printed circuit board section at the transitional region.

10. The endoscope according to claim 1, wherein the second printed circuit board section comprises at least one dimensionally-stable receiving surface to which the at least one electrical component is directly mechanically connected and electrically contacted.

11. The endoscope according to claim 10, wherein the at least one dimensionally-stable receiving surface is one of configured as part of the upper subsection or is fixed to the upper subsection.

12. The endoscope according to claim 10, wherein the at least one dimensionally-stable receiving surface has an insertion region extending in the longitudinal axial direction which is inserted into a pocket of the retaining body to fix the flexible printed circuit board on the retaining body.

13. The endoscope according to claim 12, wherein the pocket encloses the insertion region in one or more of a peripheral direction and in a radial direction.

14. The endoscope according to claim 1, wherein the retaining body has a cross-section in the form of a circular arc.

15. The endoscope according to claim 14, wherein the circular arc has a center angle of 185° to 270°.

16. The endoscope according to claim 1, wherein the retaining body comprises a groove extending along one or more of the upper side, the lower side and a side edge in which the second printed circuit board section is at least partially accommodated.

17. The endoscope according to claim 16, wherein the groove extends in the peripheral direction.

18. The endoscope according to claim 1, wherein the at least one electrical component is an electrical switch.

19. An endoscope comprising:
a shaft configured to be inserted into a body; and
a handle disposed at a proximal end of the shaft, the handle comprising a retaining body; and
an elongated, flexible printed circuit board which provides an electrical connection between at least one electrical component arranged on an outer periphery of the retaining body and an internal electrical terminal provided proximally relative to the at least one electrical component in a longitudinal axis direction of the handle;
wherein the flexible printed circuit board comprises:
a first circuit board portion arranged on the outer periphery of the retaining body, the first circuit board portion having the at least one electrical component;
a second circuit board portion extending from a first end of the first circuit board portion and arranged on an inner periphery of the retaining body; and
a third circuit board portion extending in the longitudinal axis direction from a second end of the second circuit board portion and extending proximally within a cavity in the handle toward the at least one internal electrical terminal.

20. The endoscope according to claim 19, wherein the flexible printed circuit board further comprising a U-shaped transition between the first end of the first circuit board portion and the second circuit board portion.

21. The endoscope according to claim 19, wherein the flexible printed circuit board further comprising a 90 degree transition between the second end of the second circuit board portion and the third circuit board portion.

22. The endoscope according to claim 19, wherein the at least one electrical component comprises a plurality of electrical components each arranged on the second circuit board portion.

* * * * *